(12) United States Patent
Li et al.

(10) Patent No.: US 10,689,245 B2
(45) Date of Patent: Jun. 23, 2020

(54) VERTICALLY STACKED NANOFLUIDIC CHANNEL ARRAY

(71) Applicant: International Business Machines Corporation, Armonk, NY (US)

(72) Inventors: Juntao Li, Cohoes, NY (US); Kangguo Cheng, Schenectady, NY (US); Choonghyun Lee, Rensselaer, NY (US); Peng Xu, Santa Clara, CA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 15/906,806

(22) Filed: Feb. 27, 2018

(65) Prior Publication Data
US 2019/0263655 A1    Aug. 29, 2019

(51) Int. Cl.
| B81B 1/00 | (2006.01) |
| B81C 1/00 | (2006.01) |
| H01L 21/3065 | (2006.01) |
| H01L 21/02 | (2006.01) |
| H01L 21/324 | (2006.01) |
| H01L 29/16 | (2006.01) |
| H01L 21/306 | (2006.01) |
| B01L 3/00 | (2006.01) |
| G01N 33/487 | (2006.01) |

(52) U.S. Cl.
CPC .......... *B81B 1/004* (2013.01); *B01L 3/5027* (2013.01); *B81C 1/00531* (2013.01); *B81C 1/00539* (2013.01); *H01L 21/02112* (2013.01); *H01L 21/3065* (2013.01); *H01L 21/30604* (2013.01); *H01L 21/324* (2013.01); *H01L 29/16* (2013.01); *B81B 2201/051* (2013.01); *G01N 33/48721* (2013.01)

(58) Field of Classification Search
None
See application file for complete search history.

(56) References Cited

U.S. PATENT DOCUMENTS

| 8,437,001 B2 | 5/2013 | Cheng et al. |
| 8,518,829 B2 * | 8/2013 | Dang ..................... B82Y 15/00 438/584 |

(Continued)

FOREIGN PATENT DOCUMENTS

WO    2010072861 A1    7/2010

OTHER PUBLICATIONS

Hartmann, et al., HCl selective etching of SiGe versus Si in stacks grown on Semiconductor Science and Technology, Semiconductor Science Technology, Sep. 2010, 9 Pages, vol. 25.

(Continued)

*Primary Examiner* — Long Pham
(74) *Attorney, Agent, or Firm* — Amin, Turocy & Watson, LLP

(57) ABSTRACT

Techniques regarding a vertical nanofluidic channel array are provided. For example, one or more embodiments described herein can regard an apparatus that can comprise a semiconductor substrate and a dielectric layer adjacent to the semiconductor substrate. The dielectric layer can comprise a first nanofluidic channel and a second nanofluidic channel. The second nanofluidic channel can be located between the first nanofluidic channel and the semiconductor substrate.

12 Claims, 10 Drawing Sheets

(56) References Cited

U.S. PATENT DOCUMENTS

| 9,416,001 | B2 | 8/2016 | Berenschot et al. |
| 9,570,299 | B1 | 2/2017 | Cheng et al. |
| 9,634,091 | B2 | 4/2017 | Ching et al. |
| 9,679,897 | B1 | 6/2017 | Cao et al. |
| 2012/0057163 | A1 | 3/2012 | Cheng et al. |

OTHER PUBLICATIONS

Popp, et al., Trench multiplication process by a sacrificial SiGe epitaxial Layer, 25th Annual Advanced Semiconductor Manufacturing Conference, 2014, pp. 370-372.

R. H. Chao et al., . H. Chao et al., "Bottom Channel Isolation in Nanosheet Transistors," U.S. Appl. No. 15/493,730, filed Apr. 21, 2017.

\* cited by examiner

```
┌─────────────────────────────────────────────────────────┐
│ FORMING A COLUMN ON A SEMICONDUCTOR SUBSTRATE, THE      │
│ COLUMN COMPRISING A FIRST SILICON-GERMANIUM LAYER       │  ⟵ 902
│ AND A SECOND SILICON-GERMANIUM LAYER, AND WHEREIN       │
│ THE SECOND SILICON-GERMANIUM LAYER IS POSITIONED        │
│ BETWEEN THE FIRST SILICON-GERMANIUM LAYER AND THE       │
│              SEMICONDUCTOR SUBSTRATE                    │
└─────────────────────────────────────────────────────────┘
                            │
                            ▼
┌─────────────────────────────────────────────────────────┐
│    ETCHING THE COLUMN TO REMOVE THE FIRST SILICON-      │
│  GERMANIUM LAYER AND THE SECOND SILICON-GERMANIUM       │  ⟵ 904
│ LAYER, WHEREIN THE ETCHING FORMS A FIRST NANOFLUIDIC    │
│  CHANNEL AT A POSITION OF THE FIRST SILICON-GERMANIUM   │
│ LAYER IN THE COLUMN, AND WHEREIN THE ETCHING FURTHER    │
│   FORMS A SECOND NANOFLUIDIC CHANNEL AT A POSITION OF   │
│    THE SECOND SILICON-GERMANIUM LAYER IN THE COLUMN     │
└─────────────────────────────────────────────────────────┘
```

VERTICALLY STACKED NANOFLUIDIC CHANNEL ARRAY

BACKGROUND

The subject disclosure relates to nanofluidic channel arrays, and more specifically, to arrays with nanofluidic channels stacked in one or more vertical arrangements.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, apparatuses, and/or methods regarding vertically stacked nanofluidic channel arrays are described.

According to an embodiment, an apparatus is provided. The apparatus can comprise a semiconductor substrate. The apparatus can also comprise a dielectric layer adjacent to the semiconductor substrate. The dielectric layer can comprise a first nanofluidic channel and a second nanofluidic channel. The second nanofluidic channel can be located between the first nanofluidic channel and the semiconductor substrate.

According to another embodiment, a method is provided. The method can comprise forming a column on a semiconductor substrate. The column can comprise a first silicon-germanium layer and a second silicon-germanium layer. The first silicon-germanium layer can be spaced apart from the second silicon-germanium layer. Also, the second silicon-germanium layer can be positioned between the first silicon-germanium layer and the semiconductor substrate. Further, the method can comprise etching the column to remove the first silicon-germanium layer and the second silicon-germanium layer. The etching can form a first nanofluidic channel at a position of the first silicon-germanium layer in the column. The etching can further form a second nanofluidic channel at a position of the second silicon-germanium layer in the column.

According to another embodiment, an apparatus is provided. The apparatus can comprise a semiconductor substrate. The apparatus can also comprise a dielectric layer that can be positioned adjacent to the semiconductor substrate. The apparatus can further comprise a first nanofluidic channel that can traverse through the dielectric layer. The dielectric layer can surround the first nanofluidic channel. Moreover, the apparatus can comprise a second nanofluidic channel that can traverse through the dielectric layer. The second nanofluidic channel can be positioned between the first nanofluidic channel and the semiconductor substrate.

BRIEF DESCRIPTION OF THE DRAWINGS

FIG. 9 illustrates a flow diagram of an example, non-limiting method that can facilitate manufacturing of a nanofluidic channel array, which can comprise one or more nanofluidic channels positioned in a vertical arrangement, in accordance with one or more embodiments described herein.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Nanofluidic structures can facilitate analyzing one or more characteristics of fluids confined to nanometer dimensions and are becoming increasing applicable to bionanotechnology. For example, lab-on-chip ("LOC") devices can comprise one or more nanofluidic structures to analyze fluid samples (e.g., bio-fluids). The nanofluidic structures can comprise nanofluidic channel arrays, which can further comprise an arrangement of nanofluidic channels that control and/or direct the flow of fluid samples through the nanofluidic structures. Conventional nanofluidic channel arrays arrange nanofluidic channels in a horizontal fashion. However, horizontal arrangements can limit the number of nanofluidic channels that can be comprised within the nanofluidic structures, and thereby limit operational flow rates of the nanofluidic structures.

One or more embodiments describe herein can regard a nanofluidic channel array that can comprise a plurality of nanofluidic channels in a vertical arrangement. For example, the nanofluidic channel array described herein can comprise nanofluidic channels arranged in both columns and rows. The vertical arrangement of nanofluidic channels can enable the nanofluidic channel array described herein to comprise a higher density of nanofluidic channels than can be achieved by conventional arrays. Furthermore, one or more embodiments described herein can regard methods that can facilitate manufacturing of nanofluidic channel arrays with vertically stacked nanofluidic channels.

Figure 1:
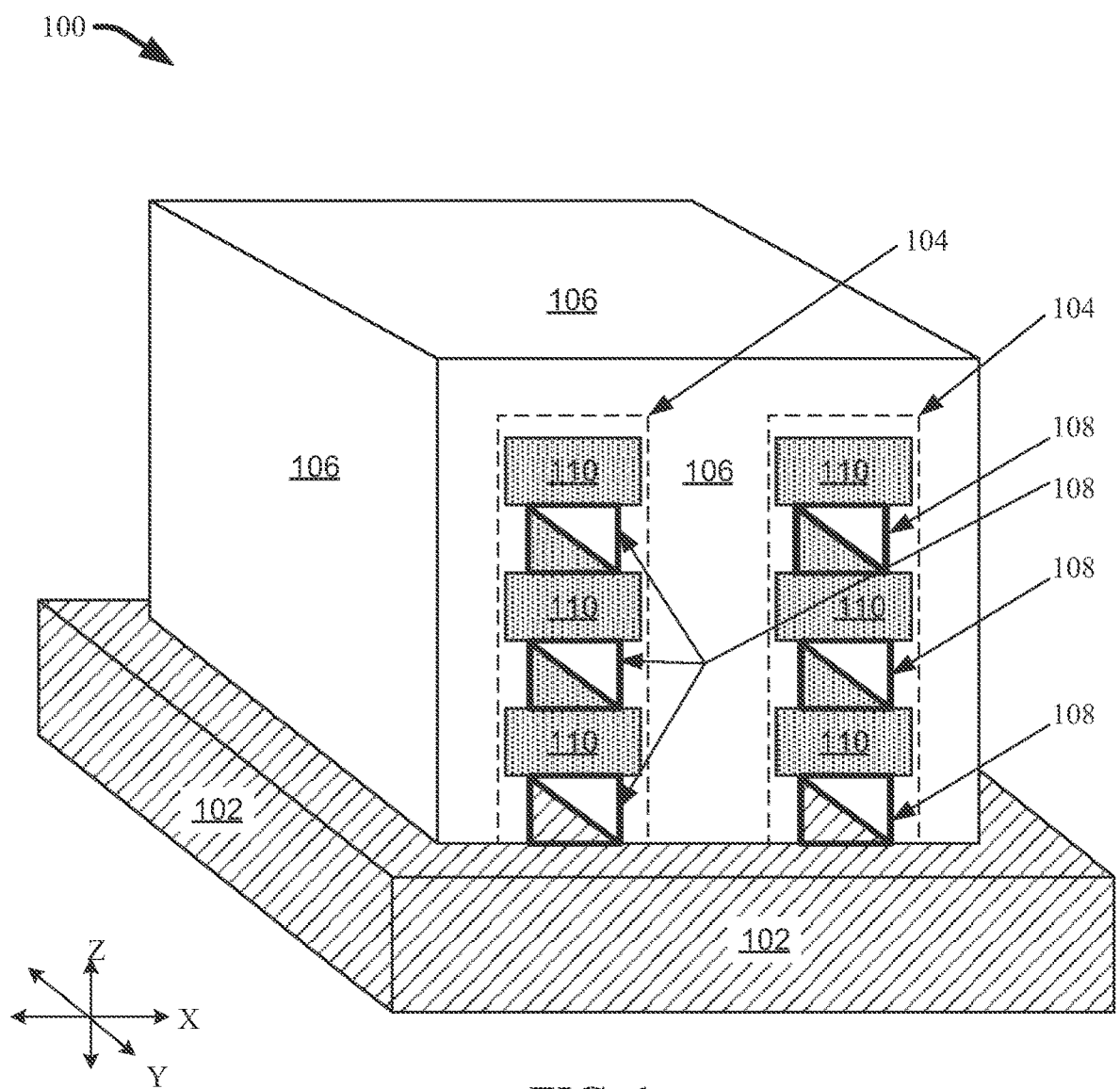
FIG. 1 illustrates a diagram of an example, non-limiting nanofluidic channel array that can comprise one or more nanofluidic channels positioned in a vertical arrangement in accordance with one or more embodiments described herein.

FIG. 1 illustrates a diagram of an example, non-limiting nanofluidic channel array 100 in accordance with one or more embodiments described herein. The nanofluidic channel array 100 can be located adjacent to a semiconductor substrate 102. For example, the nanofluidic channel array 100 can be located on top of the semiconductor substrate 102 along a "Z" axis, as shown in FIG. 1. Example materials that can comprise the semiconductor substrate 102 can include, but are not limited to: silicon, germanium, silicon carbide, carbon doped silicon, compound semiconductors (e.g., comprising elements from periodic table groups III, IV, and/or V), a combination thereof, and/or the like. For instance, the semiconductor substrate 102 can be a bulk silicon wafer and/or a silicon-on-insulator (SOI) wafer. Additionally, the semiconductor substrate 102 can comprise electronic structures such as isolation wires (not shown).

The nanofluidic channel array 100 can comprise one or more nanofluidic channel columns 104 (e.g., identified with dashed lines in FIG. 1) that can be surrounded by a dielectric layer 106. The dielectric layer 106 can comprise, for example, silicon oxide (e.g., silicon dioxide). The dielectric layer 106 can separate adjacent nanofluidic channel columns 104 and/or at least partially form a plurality of nanofluidic channels 108 comprised within the one or more nanofluidic channel columns 104. For example, the dielectric layer 106 can form one or more respective sides of the plurality of nanofluidic channels 108. The dielectric layer 106 can surround one or more of the nanofluidic channels 108 and/or encapsulate one or more of the nanofluidic channels 108 (e.g., nanofluidic channels 108 located directly on the semiconductor substrate 102).

The one or more nanofluidic channel columns 104 can comprise the plurality of nanofluidic channels 108 (e.g., delineated in FIG. 1 with bold lines) and/or one or more silicon layers 110. The plurality of nanofluidic channels 108 can be oriented in a vertical arrangement along the "Z" axis. For example, a first nanofluidic channel 108 can be positioned, along the "Z" axis, between a second nanofluidic channel 108 and the semiconductor substrate 102. Also, the second nanofluidic channel 108 can be positioned, along the "Z" axis, between a third nanofluidic channel 108 and the first nanofluidic channel 108. Thus, the nanofluidic channels 108 can form a stacked arrangement, wherein each nanofluidic channel 108 comprised within the nanofluidic channel column 104 can be positioned above another nanofluidic channel 108 and/or the semiconductor substrate 102. In other words, a plurality of nanofluidic channels 108 comprised within the nanofluidic channel column 104 can be stacked upon each other along the "Z" axis.

The plurality nanofluidic channels 108 can traverse (e.g., along a "Y" axis shown in FIG. 1) through the dielectric layer 106 substantially parallel to each other and/or the semiconductor substrate 102. The plurality of nanofluidic channels 108 can exhibit uniform dimensions as they traverse through the dielectric layer 106. Alternatively, the plurality of nanofluidic channels 108 can exhibit varying dimensions as they traverse through the dielectric layer 106. For example, the one or more of the plurality of nanofluidic channels 108 can taper as extending through the dielectric layer 106. The dielectric layer 106 can define respective first sides (e.g., left sides) and/or respective second sides (e.g., right sides) of the plurality of nanofluidic channels 108. Further, the respective first sides of the plurality of nanofluidic channels 108 can be opposite the respective second sides of the plurality of nanofluidic channels 108.

The one or more silicon layers 110 can comprise intrinsic silicon and/or an intrinsic silicon composite. The one or more silicon layers 110 can traverse the length (e.g., along the "Y" axis) of the plurality of nanofluidic channels 108 and can form at least a portion of respective nanofluidic channels 108. For example, the one or more silicon layers 110 can define respective third sides (e.g., top sides) of the plurality of nanofluidic channels 108 and/or respective fourth sides (e.g., bottom sides) of the plurality of nanofluidic channels 108. In one or more embodiments, the nanofluidic channel 108 of the nanofluidic channel column 104 that is nearest the semiconductor substrate 102 can have a fourth side (e.g., a bottom side) defined by the semiconductor substrate 102.

While FIG. 1 shows one or more nanofluidic channel columns 104 comprising three nanofluidic channels 108, the architecture of the nanofluidic channel columns 104 is not so limited. For example, one or more nanofluidic channel columns 104 can comprise two or more nanofluidic channels 108. Additionally, adjacent nanofluidic channel columns 104 can have the same number of nanofluidic channels 108 or a different number of nanofluidic channels 108. Additionally, while FIG. 1 shows rectangular nanofluidic channels 108, the architecture of the nanofluidic channels 108 is also not so limited. Example shapes that can characterize the nanofluidic channels 108 can include, but are not limited to: circular, square, rectangular, polygonal, a combination thereof, and/or the like.

The plurality of nanofluidic channels 108 can have uniform dimension with respect to each other and/or varying dimensions with respect to each other. For example, all the nanofluidic channels 108 from the plurality of nanofluidic channels 108 can have the same length (e.g., along the "Y" axis), width (e.g., along the "X" axis), and/or height (e.g., along the "Z" axis). In another example, one or more nanofluidic channels 108 (e.g., comprising a first nanofluidic channel column 104) can have different dimensions than one or more other nanofluidic channels 108 (e.g., comprising a second nanofluidic channel column 104). The plurality of nanofluidic channels 108 can have an example, non-limiting length (e.g., along the "Y" axis) greater than or equal to 100 nanometers (nm) and less than or equal to 10,000 nm. Also, the plurality of nanofluidic channels 108 can have an example, non-limiting width (e.g., along the "X" axis) greater than or equal to 10 nm and less than or equal to 100 nm. Further, the plurality of nanofluidic channels 108 can have an example, non-limiting height (e.g., along the "Z" axis) greater than or equal to 5 nm and less than or equal to 30 nm.

In one or more embodiments, the nanofluidic channel array 100 can comprise a plurality of nanofluidic channel columns 104, wherein the nanofluidic channel columns 104 can be positioned adjacent to each along an "X" axis, as shown if FIG. 1. The dielectric layer 106 can separate adjacent nanofluidic channel columns 104. Additionally, dimensions regarding a subject nanofluidic channel column 104 can be independent of dimensions regarding another nanofluidic channel column 104. For example, the dimensions of a first nanofluidic channel column 104 comprised within the nanofluidic channel array 100 can be the same as the dimensions of another nanofluidic channel column 104 comprised within the nanofluidic channel array 100. In another example, the dimensions of a first nanofluidic channel column 104 comprised within the nanofluidic channel array 100 can be different (e.g., greater than or less) than the dimensions of another nanofluidic channel column 104 comprised within the nanofluidic channel array 100.

The vertical arrangement (e.g., along the "Z" axis) of the plurality of nanofluidic channels 108 enables the nanofluidic channel array 100 to have a high density of nanofluidic channels 108. For example, a first side of the dielectric layer 106 can comprise (e.g., surround and/or define) greater than or equal to 10 and less than or equal to 100 nanofluidic channels 108 per micrometer along the "X" axis.

Figure 2:
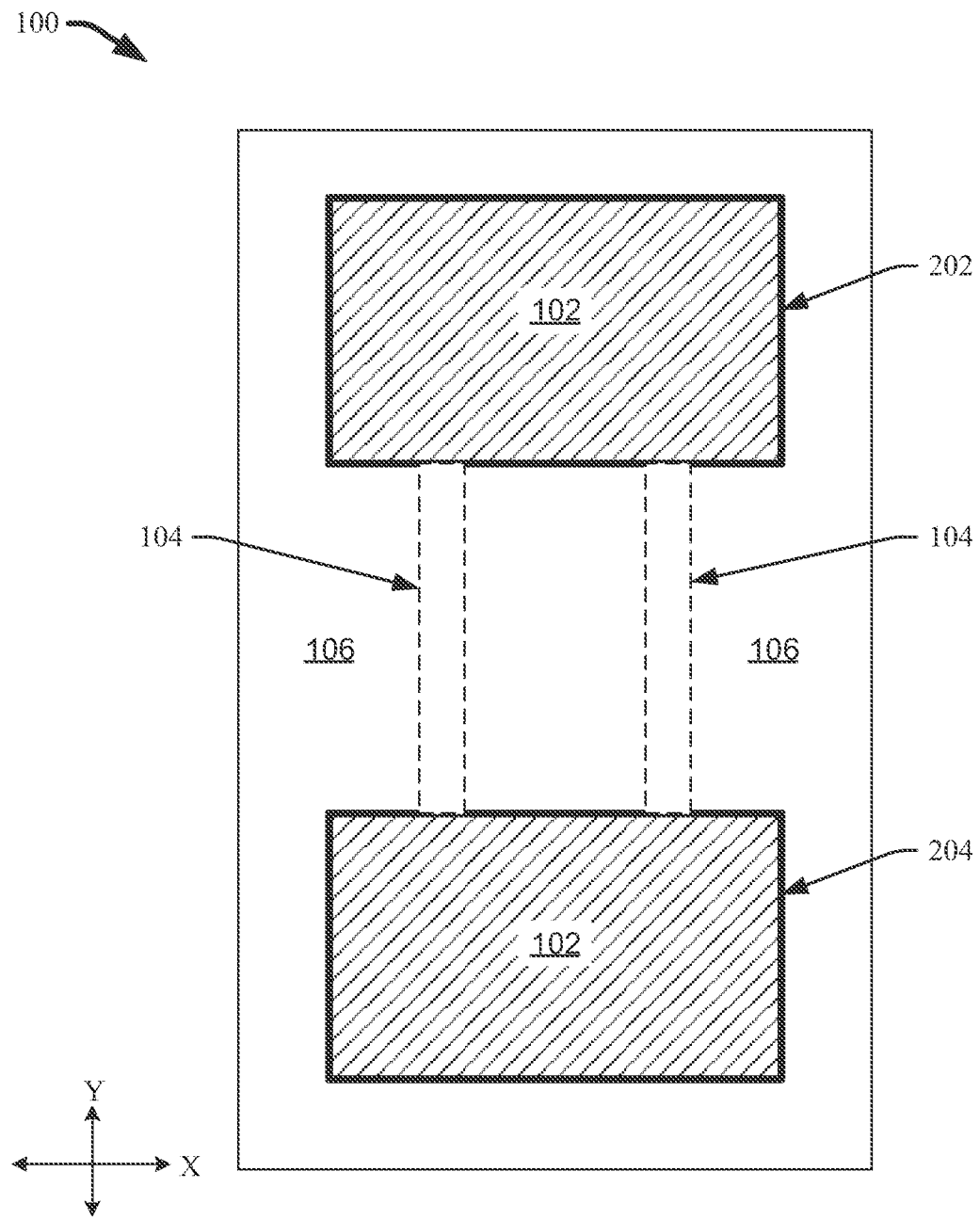
FIG. 2 illustrates a diagram of an example, non-limiting nanofluidic channel array that can facilitate fluid communication between a plurality of reservoirs in accordance with one or more embodiments described herein.

FIG. 2 illustrates a diagram of the example, non-limiting nanofluidic channel array 100 in fluid communication with a first reservoir 202 and/or a second reservoir 204 in accordance with one or more embodiments described herein. Repetitive description of like elements employed in other embodiments described herein is omitted for sake of brevity. FIG. 2 illustrates a top view of the nanofluidic channel array 100.

As shown in FIG. 2, the nanofluidic channel array 100 can connect a first reservoir 202 (e.g., delineated by bold lines in FIG. 2) to a second reservoir 204 (e.g., also delineated by bold lines in FIG. 2). The first reservoir 202 and the second reservoir 204 can be located on the semiconductor substrate 102 and can be hollow spaces, which can contain a fluid. The first reservoir 202 and the second reservoir 204 can be defined by the semiconductor substrate 102 and/or the dielectric layer 106. For example, the semiconductor substrate 102 can form a bottom side of the first reservoir 202 and/or the second reservoir 204. The dielectric layer 106 can surround the first reservoir 202, thereby forming the vertical sides of the first reservoir 202 (e.g., the front side, the back side, the left side, and/or the right side). Similarly, the dielectric layer 106 can surround the second reservoir 204, thereby forming the vertical sides of the second reservoir 204 (e.g., the front side, the back side, the left side, and/or the right side). A top side of the first reservoir 202 and/or second reservoir 204 can remain open (e.g., as shown in FIG. 2), can further be formed by the dielectric layer 106, and/or can be in fluidic communication with another feature of the nanofluidic channel array 100 (e.g., a fluid inlet and/or a fluid outlet).

The dimensions of the first reservoir 202 can be independent of the dimensions of the second reservoir 204. For example, the first reservoir 202 can have the same dimensions as the second reservoir 204. In another example, the first reservoir 202 can have different dimensions than the second reservoir 204. While FIG. 2 shows a rectangular first reservoir 202 and/or a rectangular second reservoir 204, the architecture of the first reservoir 202 and/or the second reservoir 204 is not so limited. Example shapes that can characterize the first reservoir 202 and/or the second reservoir 204 can include, but are not limited to: circular, square, rectangular, polygonal, a combination thereof, and/or the like. Additionally, the nanofluidic channel array 100 can be in fluid communication with one or more additional reservoirs. For example, the nanofluidic channel array 100 can connect a third reservoir (not shown) with the first reservoir 202 and/or the second reservoir 204, wherein the third reservoir can exhibit similar features and/or functions as the first reservoir 202 and/or the second reservoir 204.

The dashed lines in FIG. 2 can delineate positions of the one or more nanofluidic channel columns 104 within the dielectric layer 106. As shown in FIG. 2, the nanofluidic channel columns 104, and thereby the plurality of nanofluidic channels 108, can extend through the dielectric layer 106 from the first reservoir 202 to the second reservoir 204. The nanofluidic channel columns 104 can extend into one or more sides of the first reservoir 202 and one or more sides of the second reservoir 204. Thus, the first reservoir 202 can be in fluid communication with the second reservoir 204 via the plurality of nanofluidic channels 108.

Figure 3:
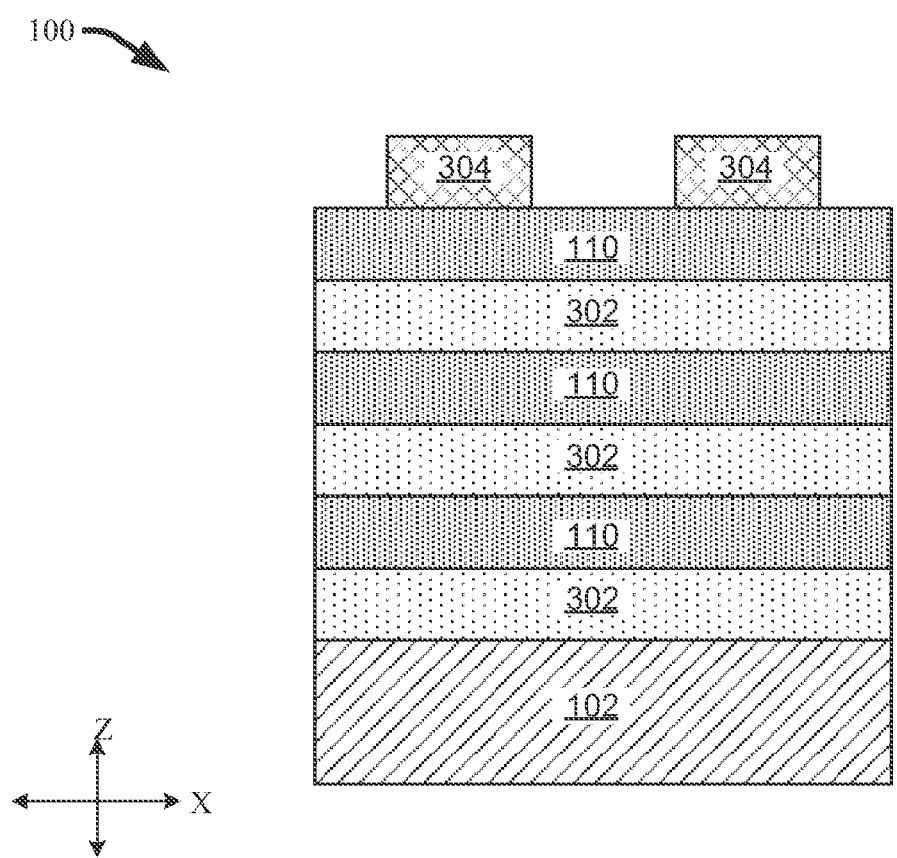
FIG. 3 illustrates a diagram of an example, non-limiting cross-sectional view of a nanofluidic channel array during a first stage of manufacturing in accordance with one or more embodiments described herein.

FIG. 3 illustrates a diagram of the example, non-limiting nanofluidic channel array 100 during a first stage of manufacturing in accordance with one or more embodiments described herein. Repetitive description of like elements employed in other embodiments described herein is omitted for sake of brevity. FIG. 3 illustrates a cross-sectional view of the nanofluidic channel array 100 during the first stage of manufacturing.

As shown in FIG. 3, one or more silicon-germanium layers 302 can be deposited on top of the semiconductor substrate 102 along the "Z" axis, wherein the one or more silicon layers 110 can separate adjacent silicon-germanium layers 302. The silicon-germanium layers 302 can be a composition comprising silicon and germanium. For example, the one or more silicon-germanium layers 302 can comprise 20% germanium and 80% silicon. While FIG. 3 illustrates a bottom-most silicon-germanium layer 302 located directly adjacent to the semiconductor substrate 102, the architecture of the nanofluidic channel array 100 during the first stage of manufacturing is not so limited. For example, a silicon layer 110 can be located between the bottom-most silicon-germanium layer 302 and the semiconductor substrate 102.

In one or more embodiments, the one or more silicon-germanium layers 302 can be grown from silicon comprising the semiconductor substrate 102 and/or the one or more silicon layers 110. Thus, the one or more silicon-germanium layers 302 can be have the same, and/or substantially similar, crystal orientation as the semiconductor substrate 102 and/or the one or more silicon layers 110. For example, the one or more silicon-germanium layers 302 can be deposited/grown on the semiconductor substrate 102 and/or one or more of the silicon layers 110 via molecular-beam epitaxy ("MBE"), low-pressure chemical vapor deposition ("LPCVD"), and/or ultra-high-vacuum chemical vapor deposition ("UHV-CVD"). For example, the one more silicon-germanium layers 302 can be epitaxial layers.

While FIG. 3 shows three silicon-germanium layers 302, the architecture of the nanofluidic channel array 100 during the first stage of manufacturing is not so limited. For example, two or more (e.g., four or more) silicon-germanium layers 302 can be deposited and/or grown on the semiconductor substrate 102 and/or the one or more silicon layers 110. The number of silicon-germanium layers 302 deposited and/or grown can depend on the number of nanofluidic channels 108 desired in the nanofluidic channel array 100.

Further, one or more masking layers 304 can be patterned on top the stack of silicon-germanium layers 302 and/or silicon layers 110. The one or more masking layers 304 can comprise, for example, a hardmask material (e.g., silicon nitride), a polymer material, and/or an organic material. For example, the one or more masking layers 304 can be patterned as a part of a photolithography process. Further, the one or more masking layers 304 can be patterned onto a silicon layer 110 that is furthest from the semiconductor substrate 102 along the "Z" axis (e.g., the top-most silicon layer 110). The one or more masking layers 304 can define the position, width (e.g., along the "X" axis), and/or length (e.g., along the "Y" axis) of the one or more nanofluidic channel columns 104.

Figure 4A:
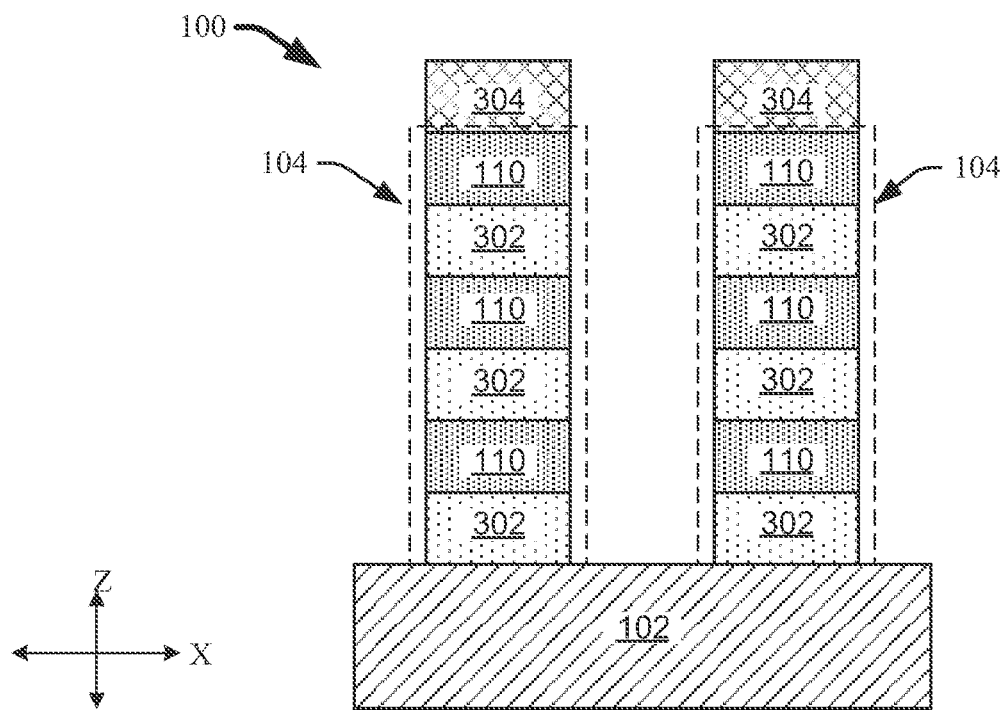
FIG. 4A illustrates a diagram of an example, non-limiting cross-sectional view of a nanofluidic channel array during a second stage of manufacturing in accordance with one or more embodiments described herein.

FIG. 4A illustrates a diagram of the example, non-limiting nanofluidic channel array 100 during a second stage of manufacturing in accordance with one or more embodiments described herein. Repetitive description of like elements employed in other embodiments described herein is omitted for sake of brevity. FIG. 4A shows a cross-sectional view of the nanofluidic channel array 100 during the second stage of manufacturing.

As shown in FIG. 4A, one or more etching processes can remove one or more portions of the one or more silicon-germanium layers 302 and/or the one or more silicon layers 110. For example, the one or more etching processes can remove exposed portions that were not protected by the one or more masking layers 304 along the "Z" axis. The one or more etching processes can comprise, for example, a reactive ion etch ("RIE"). Further, the etching can form the general structure of the one or more nanofluidic channel columns 104 (e.g., delineated by dashed lines in FIG. 4A). For example, the one or more etching processes (e.g., RIE) can comprise deep etching extending to the semiconductor substrate 102. In another example, the one or more etching processes can comprise sidewall image transfer ("SIT") techniques.

Figure 4B:
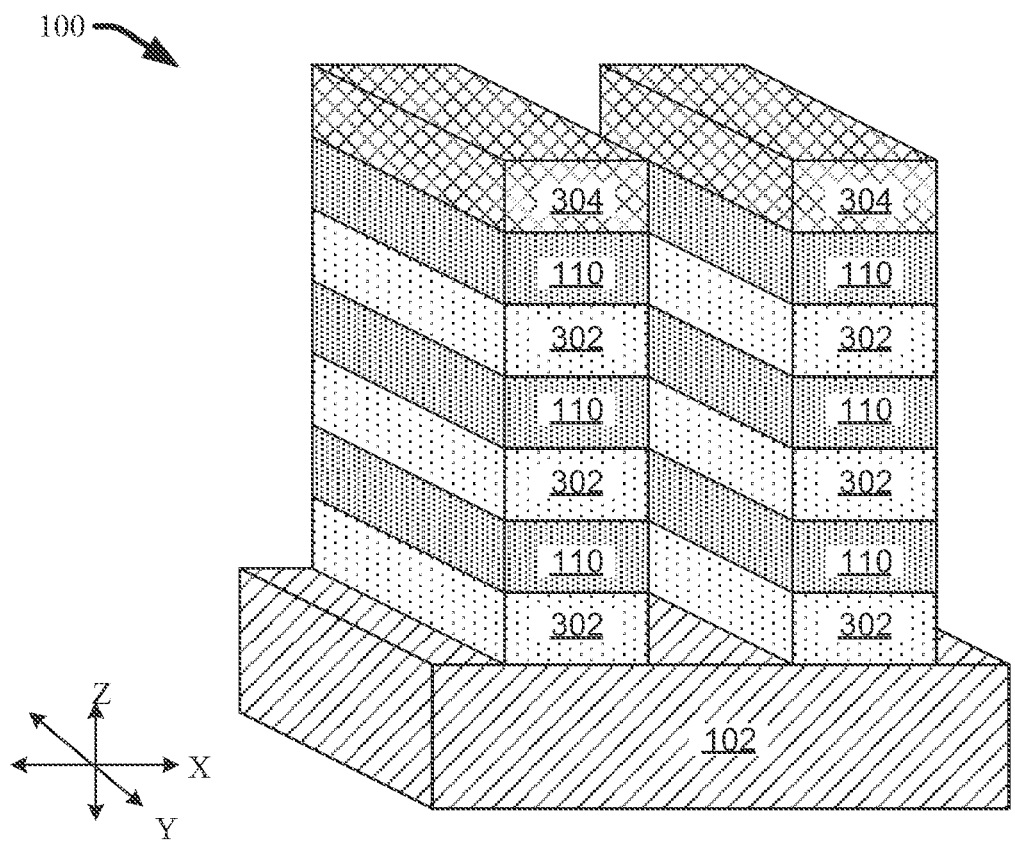
FIG. 4B illustrates a diagram of an example, non-limiting nanofluidic channel array during a second stage of manufacturing in accordance with one or more embodiments described herein.

FIG. 4B illustrates another diagram of the example, non-limiting nanofluidic channel array 100 during the second stage of manufacturing in accordance with one or more embodiments described herein. Repetitive description of like elements employed in other embodiments described herein is omitted for sake of brevity. FIG. 4B shows the nanofluidic channel array 100 at a 45-degree angle during the second stage of manufacturing. As shown in FIG. 4B, the one or more etching processes can define a width (e.g., along the "X" axis) and a length (e.g., along the "Y" axis) of the one or more nanofluidic channel columns 104.

Figure 5A:
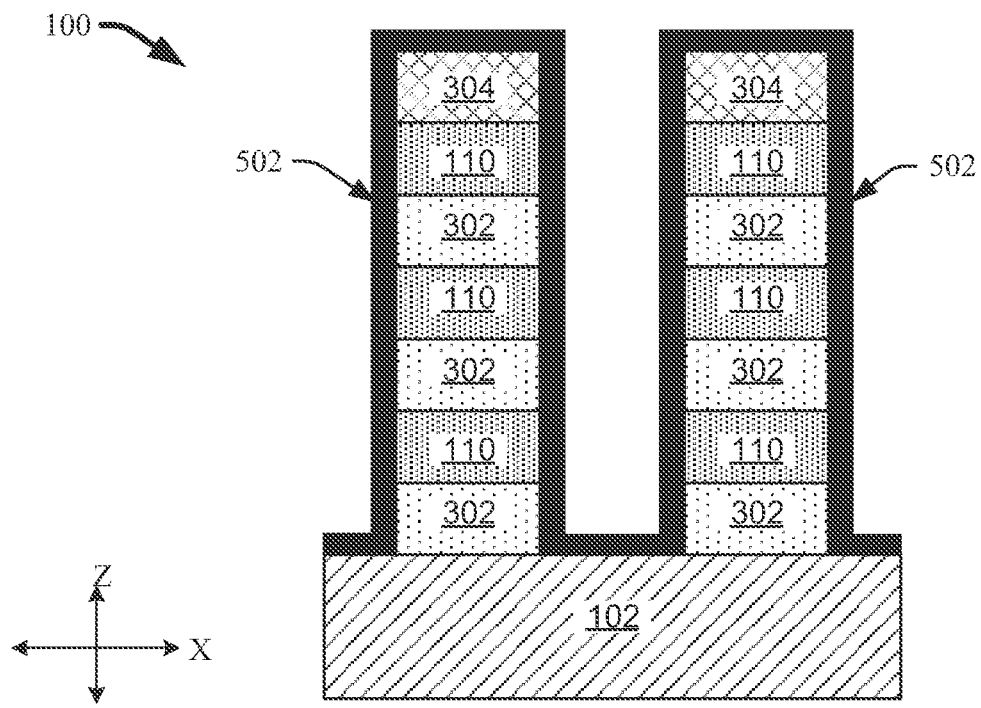
FIG. 5A illustrates a diagram of an example, non-limiting cross-sectional view of a nanofluidic channel array during a third stage of manufacturing in accordance with one or more embodiments described herein.

FIG. 5A illustrates a diagram of the example, non-limiting nanofluidic channel array 100 during a third stage of manufacturing in accordance with one or more embodiments described herein. Repetitive description of like elements employed in other embodiments described herein is omitted for sake of brevity. FIG. 5A shows a cross-sectional view of the nanofluidic channel array 100 during the third stage of manufacturing. As shown in FIG. 5A, a germanium dioxide layer 502 can be deposited over the one or more masking layers 304, the one or more silicon layers 110, the one or more silicon-germanium layers 302, and/or the semiconductor substrate 102. A thickness of the germanium dioxide layer 502 can be greater than or equal to 3 nm and less than or equal to 20 nm. The germanium dioxide layer 502 can be deposited using, for example, one or more chemical vapor deposition (CVD) techniques, such as atomic layer deposition ("ALD").

Figure 5B:
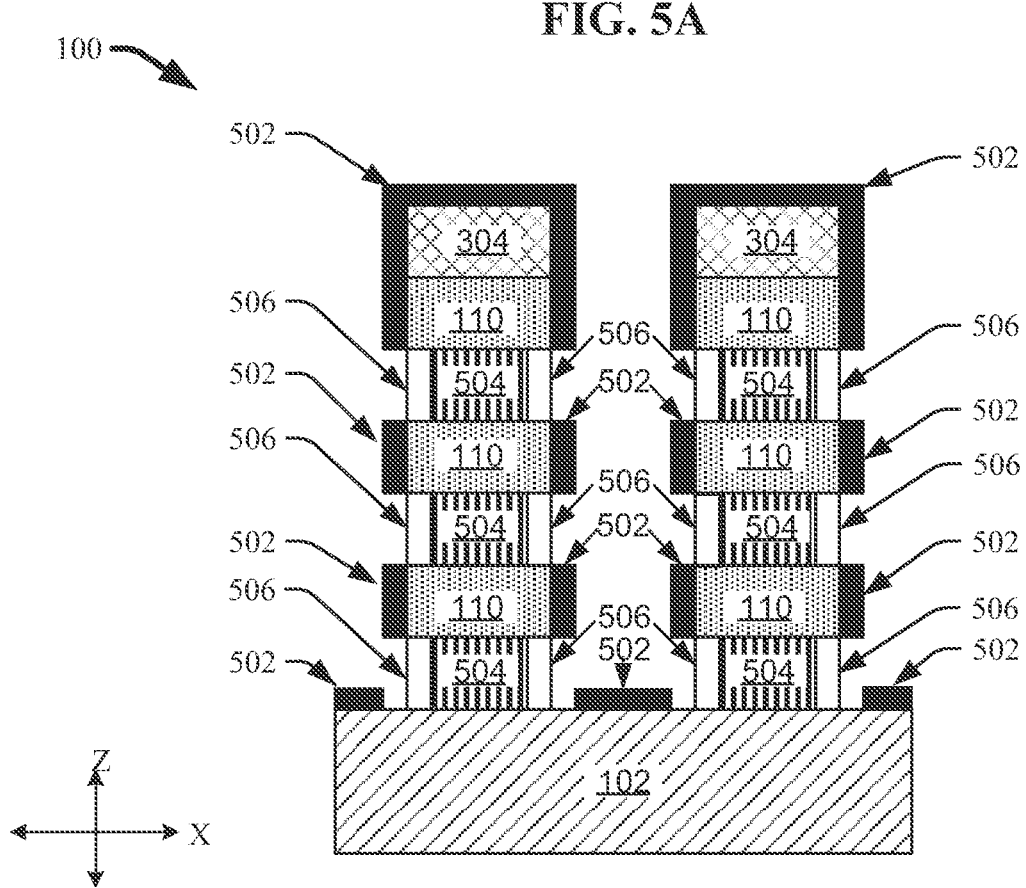
FIG. 5B illustrates a diagram of an example, non-limiting cross-sectional view of a nanofluidic channel array during a fourth stage of manufacturing in accordance with one or more embodiments described herein.

FIG. 5B illustrates a diagram of the example, non-limiting nanofluidic channel array 100 during a fourth stage of manufacturing in accordance with one or more embodiments described herein. Repetitive description of like elements employed in other embodiments described herein is omitted for sake of brevity. FIG. 5B shows a cross-sectional view of the nanofluidic channel array 100 during the fourth stage of manufacturing.

During the fourth stage of manufacturing, the nanofluidic channel array 100 can be subject to one or more annealing processes, such as spike annealing. The annealing (e.g., spike annealing) can be conducted in an atmosphere comprising an inert gas, such as a nitrogen gas atmosphere. Further, the annealing can be performed at a temperature greater than or equal to 500 degrees Celsius (° C.) and less than or equal to 900° C. (e.g., 700° C.). The annealing can cause the one or more silicon-germanium layers 302 to react with the germanium dioxide layer 502 to form one or more concentrated silicon-germanium layers 504 and/or one or more silicon dioxide layers 506.

The one or more silicon dioxide layers 506 can be located adjacent to the one or more concentrated silicon-germanium layers 504. For example, respective concentrated silicon-germanium layers 504 can be located between silicon dioxide layers 506 along the "X" axis, wherein each concentrated silicon-germanium layer 504 can be located adjacent to two silicon dioxide layers 506. The thickness of the silicon dioxide layers 506 can be substantially similar to the thickness of the germanium dioxide layer 502.

The one or more concentrated silicon-germanium layers 504 can have an increased concentration of germanium than the one or more silicon-germanium layers 302. For example, wherein the one or more silicon-germanium layers 302 comprise 20% germanium and 80% silicon, the one or more concentrated silicon-germanium layers 504 can comprise 40% germanium and 60% silicon.

The annealing can facilitate an oxidation reaction between the one or more silicon-germanium layers 302 and the germanium dioxide layer 502, wherein silicon in the one or more silicon-germanium layers 302 is oxidized to form the one or more silicon dioxide layers 506. For example, the oxidation reaction can be characterized by the following formula:

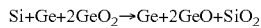

$$Si+Ge+2GeO_2 \rightarrow Ge+2GeO+SiO_2$$

The germanium product can be comprised within the one or more concentrated silicon-germanium layers 504, the germanium oxide product can be a volatile species, and/or the silicon dioxide product can form the one or more silicon dioxide layers 506. As a result of the oxidation induced by the one or more annealing processes, the respective widths (e.g., along the "X" axis) of the one or more concentrated silicon-germanium layers 504 can be less than the respective widths (e.g., along the "X" axis) of the one or more silicon-germanium layers 302. However, portions of the germanium dioxide layer 502 that were not in contact with the one or more silicon-germanium layers 302 can remain unreacted. For example, portions of the germanium dioxide layer 502 adjacent to the one or more masking layers 304, the one or more silicon layers 110, and/or the semiconductor substrate 102 can remain unreacted.

Figure 6A:
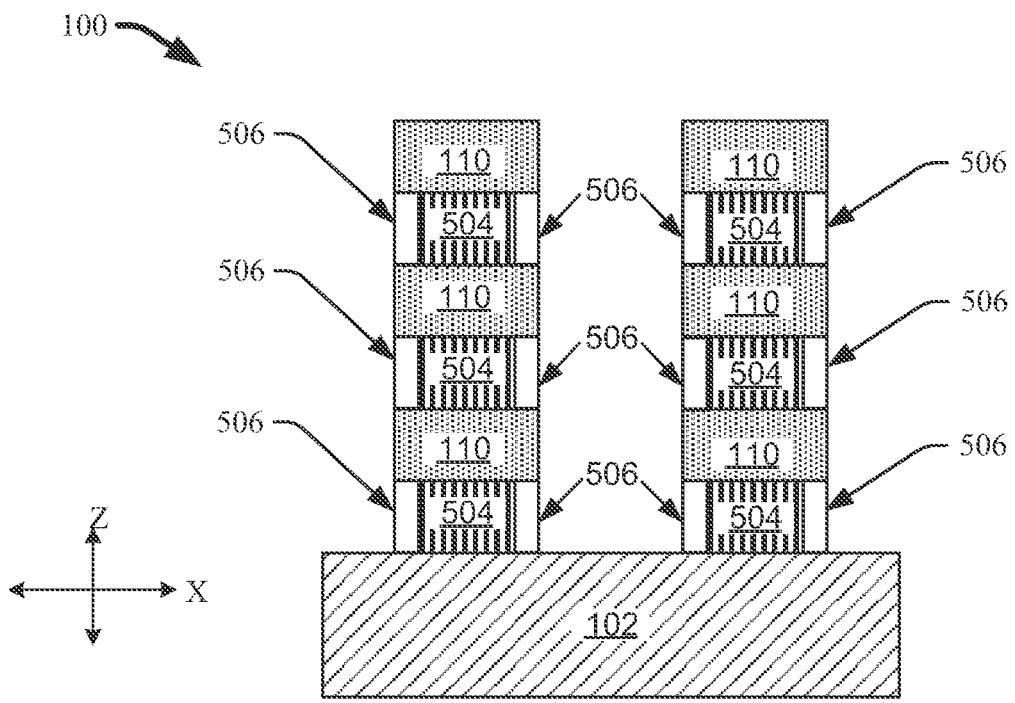
FIG. 6A illustrates a diagram of an example, non-limiting cross-sectional view of a nanofluidic channel array during a fifth stage of manufacturing in accordance with one or more embodiments described herein.

FIG. 6A illustrates a diagram of the example, non-limiting nanofluidic channel array 100 during a fifth stage of manufacturing in accordance with one or more embodiments described herein. Repetitive description of like elements employed in other embodiments described herein is omitted for sake of brevity. FIG. 6A shows a cross-sectional view of the nanofluidic channel array 100 during the fifth stage of manufacturing. As shown in FIG. 6A, the unreacted portions of the germanium dioxide layer 502 and the one or more masking layers 304 can be removed (e.g., stripped) from the nanofluidic channel array 100.

Figure 6B:
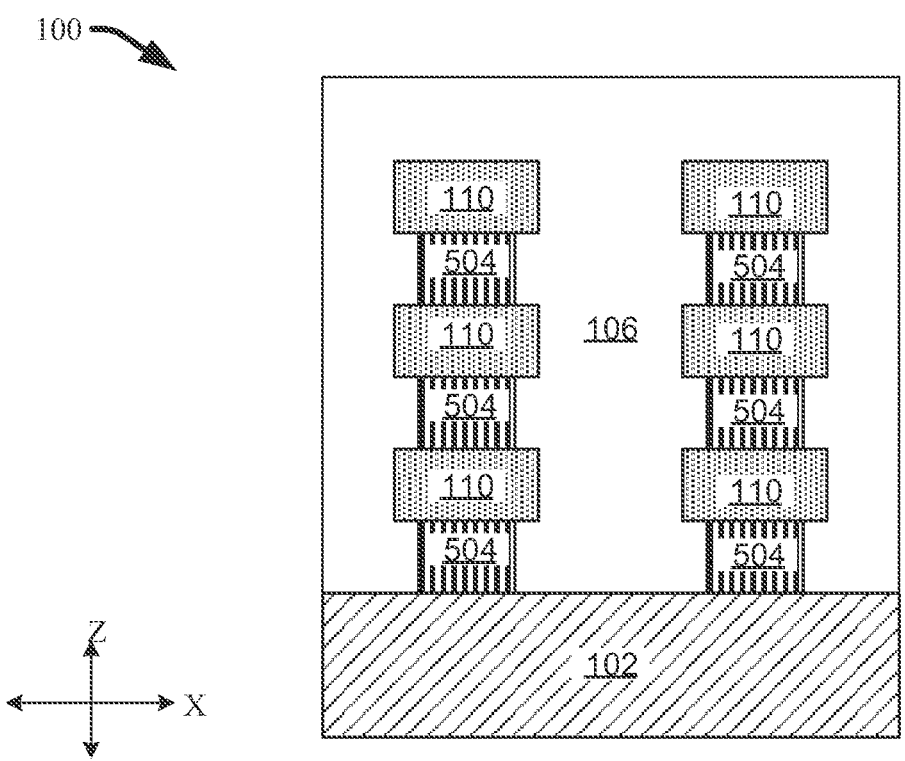
FIG. 6B illustrates a diagram of an example, non-limiting cross-sectional view of a nanofluidic channel array during a sixth stage of manufacturing in accordance with one or more embodiments described herein.

FIG. 6B illustrates a diagram of the example, non-limiting nanofluidic channel array 100 during a sixth stage of manufacturing in accordance with one or more embodiments described herein. Repetitive description of like elements employed in other embodiments described herein is omitted for sake of brevity. FIG. 6B shows a cross-sectional view of the nanofluidic channel array 100 during the sixth stage of manufacturing.

The dielectric layer 106 can be deposited onto the semiconductor substrate 102 such that the dielectric layer 106 surrounds the one or more silicon layers 110, the one or more concentrated silicon-germanium layers 504, and/or the one or more silicon dioxide layers 506. For example, the dielectric layer 106 can be blanket deposited (e.g., via CVD). As shown in FIG. 6B, wherein the dielectric layer 106 is silicon dioxide, the one or more silicon dioxide layers 506 can become a part of the dielectric layer 106. Additionally, the dielectric layer 106 can be planarized using, for example, chemical mechanical planarization ("CMP") techniques.

Subsequent to depositing the dielectric layer 106, the one or more concentrated silicon-germanium layers 504 can be etched away to form the plurality of nanofluidic channels 108 (e.g., as shown in FIG. 1). For example, the one or more concentrated silicon-germanium layers 504 can be removed via a selective etching process, which can, for example, include gas phase hydrogen fluoride etch, a wet etch process containing a mix of ammonia and hydrogen peroxide, a dry etch such as plasma etch, a combination thereof, and/or the like. Additionally, the first reservoir 202 and/or the second reservoir 204 can be formed via another etching of the dielectric layer 106. For example, another masking layer 304 can be patterned on the dielectric layer 106, wherein exposed portions of the dielectric layer 106 can be subject to a deep etching process that can define the first reservoir 202 and/or the second reservoir 204 within the dielectric layer 106 (e.g., as shown in FIG. 2).

Figure 7A:
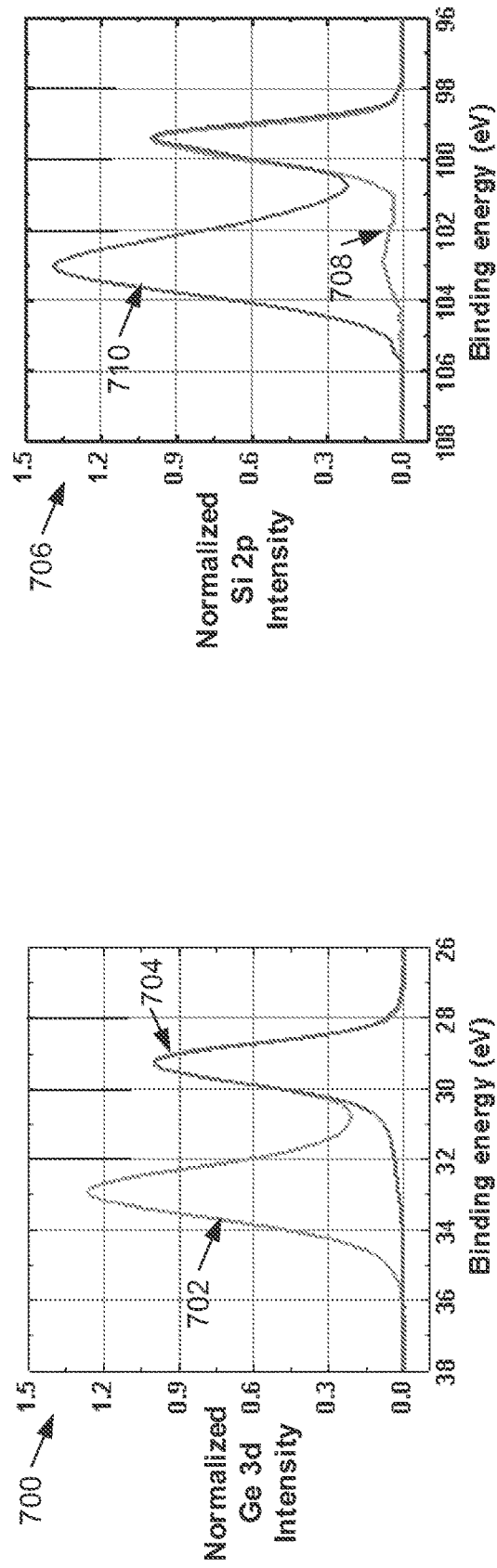
FIG. 7A illustrates a diagram of an example, non-limiting graph that depicts one or more characteristics of one or more materials comprised within a nanofluidic channel array in accordance with one or more embodiments described herein.

FIG. 7A illustrates a diagram of an example, non-limiting graph 700 that can depict one or more characteristics of one or more materials comprising the nanofluidic channel array 100 in accordance with one or more embodiments described herein. Repetitive description of like elements employed in other embodiments described herein is omitted for sake of brevity. For example, graph 700 depicts normalized germanium $3d$ orbitals verse binding energy; wherein the first line 702 represents before the annealing processes described herein, and the second line 704 represents after the annealing processes described herein. Graph 700 shows that the annealing process described herein reduces germanium dioxide subject to reactivity.

Figure 7B:
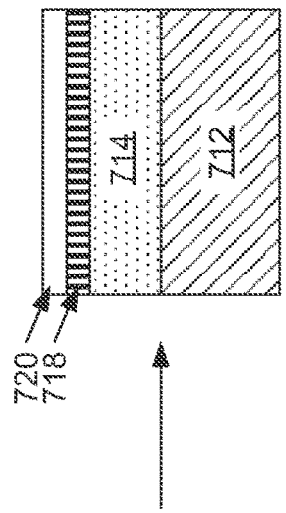
FIG. 7B illustrates a diagram of an example, non-limiting graph that depicts one or more characteristics of one or more materials comprised within a nanofluidic channel array in accordance with one or more embodiments described herein.

FIG. 7B illustrates a diagram of an example, non-limiting graph 706 that can depict one or more characteristics of one or more materials comprising the nanofluidic channel array 100 in accordance with one or more embodiments described herein. Repetitive description of like elements employed in other embodiments described herein is omitted for sake of brevity. For example, graph 706 depicts normalized silicon $2p$ orbitals verse binding energy; wherein the third line 708 represents before the annealing processes described herein, and the fourth line 710 represents after the annealing process described herein. Graph 706 shows that the annealing process described herein form silicon dioxide products.

Figure 7C:
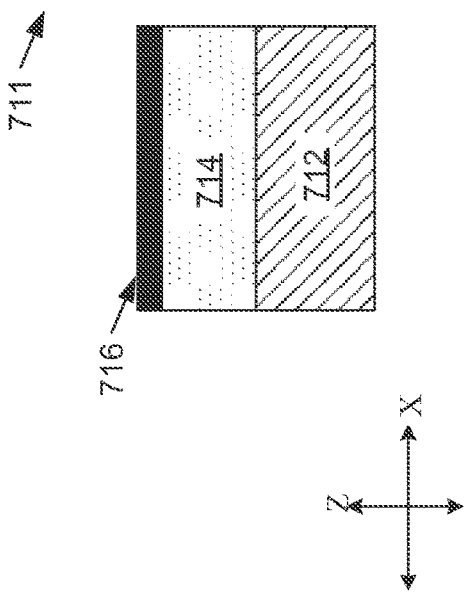
FIG. 7C illustrates a diagram of an example, non-limiting oxidation process that can be exhibited by one or more materials comprised within a nanofluidic channel array during manufacturing of the channel array in accordance with one or more embodiments described herein.

FIG. 7C illustrates a diagram of an example, non-limiting oxidation 711 of silicon during the one or more annealing processes described herein in accordance with one or more embodiments described herein. Repetitive description of like elements employed in other embodiments described herein is omitted for sake of brevity. FIG. 7C depicts an example reaction to exemplify the oxidation exhibited by the one or more annealing processes described herein.

FIG. 7C shows a reactant structure comprising an example semiconductor substrate 712 (e.g., comprising the same features and/or functions as semiconductor substrate 102), an example silicon-germanium layer 714 (e.g., comprising the same features and/or functions as silicon-germanium layer 302), and/or an example germanium dioxide layer 716 (e.g., comprising the same features and/or functions as germanium dioxide layer 502). The example silicon-germanium layer 714 can comprise, for example, 20 percent germanium and 80 percent silicon. The example silicon-germanium layer 714 can have a thickness (e.g., along the "Z" axis) of 20 nanometers (nm) and the example germanium dioxide layer 716 can have a thickness (e.g., along the "Z" axis) of 3 nm. The reactant structure can be subject to an annealing process in a nitrogen gas atmosphere at a temperature of 700° C.

The annealing process can result in the product structure shown in FIG. 7C. The product structure can comprise the example semiconductor substrate 102, the example silicon-germanium layer 302, an example concentrated silicon-germanium layer 718 (e.g., comprising the same features and/or functions as concentrated silicon-germanium layer 504), and an example silicon dioxide layer 720 (e.g., comprising the same features and/or functions as silicon dioxide layer 506). The example concentrated silicon-germanium layer 718 can comprise, for example, 40 percent germanium and 60 percent silicon. The example silicon-germanium layer 714 can have a thickness (e.g., along the "Z" axis) of 16 nm, the example concentrated silicon-germanium layer 718 can have a thickness (e.g., along the "Z" axis) of 3 nm, and the example silicon dioxide layer 720 can have a thickness (e.g., along the "Z" axis) of 3 nm. As shown in FIGS. 7A-7C, silicon comprised within the silicon-germanium layers 302 can be oxidized by the one or more annealing processes described herein due at least to lower Gibbs free energy.

Figure 8:
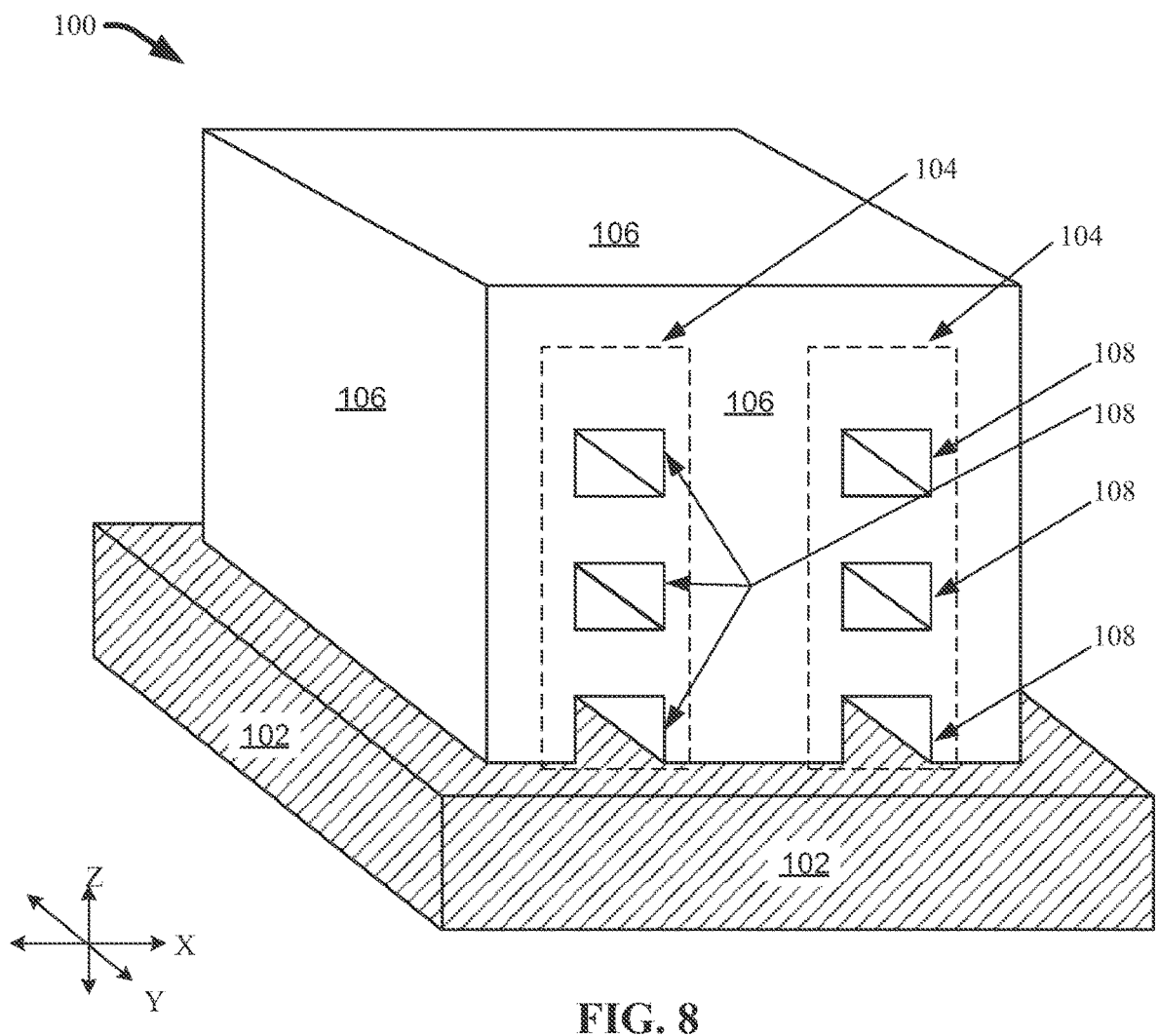
FIG. 8 illustrates a diagram of an example, non-limiting nanofluidic channel array that can comprise one or more nanofluidic channels positioned in a vertical arrangement in accordance with one or more embodiments described herein.

FIG. 8 illustrates a diagram of an example, non-limiting nanofluidic channel array 100 that has been subject to thermal oxidation in accordance with one or more embodiments described herein. Repetitive description of like elements employed in other embodiments described herein is omitted for sake of brevity. In one or more embodiments, the nanofluidic channel array 100 (e.g., of FIG. 1) can undergo a thermal oxidation treatment, which can oxidize the one or more silicon layers 110 to form silicon dioxide. Wherein the dielectric layer 106 is silicon dioxide, the silicon dioxide formed from the silicon layers 110 can become a part of the dielectric layer 106, as shown in FIG. 8.

FIG. 9 illustrates a flow diagram of an example, non-limiting method 900 that can facilitate manufacturing of the nanofluidic channel array 100 in accordance with one or more embodiments described herein. Repetitive description of like elements employed in other embodiments described herein is omitted for sake of brevity.

At 902, the method 900 can comprise forming one or more columns (e.g., one or more nanofluidic channel columns 104) on a semiconductor substrate 102. The one or more columns can comprise a first silicon-germanium layer (e.g., concentrated silicon-germanium layer 504) and/or a second silicon-germanium layer (e.g., concentrated silicon-germanium layer 504). Also, the second silicon-germanium layer (e.g., concentrated silicon-germanium layer 504) can be position between the first silicon-germanium layer (e.g., concentrated silicon-germanium layer 504) and the semiconductor substrate 102 (e.g., along the "Z" axis). Further, the one or more columns (e.g., one or more nanofluidic channel columns 104) can comprise additional silicon-germanium layers (e.g., concentrated silicon-germanium layer 504). Moreover, the one or more columns (e.g., one or more nanofluidic channel columns 104) can comprise one or more silicon layers 110 that can separate the first silicon-germanium layer (e.g., concentrated silicon-germanium layer 504) and the second silicon-germanium layer (e.g., concentrated silicon-germanium layer 504).

The forming at 902 can comprise depositing and/or growing one or more silicon-germanium layers 302 and/or one or more silicon layers 110 onto the semiconductor substrate 102 as illustrate and/or described herein with regard to FIG. 3. Also, the forming at 902 can further comprise etching the one or more silicon-germanium layers 302 and/or one or more silicon layers 110 to define a structure of the one or more columns (e.g., one or more nanofluidic channel columns 104) as illustrated and/or described herein with regard to FIGS. 4A and/or 4B. Moreover, the forming at 902 can comprise forming one or more concentrated silicon-germanium layers 504 by depositing a germanium dioxide layer 502 onto the one or more columns (e.g., one or more nanofluidic channel columns 104) and subjecting the one or more columns (e.g., one or more nanofluidic channel columns 104) to an annealing process as illustrated and/or described herein with regard to FIGS. 5A and/or 5B. For example, the annealing process can facilitate a reaction between the germanium dioxide layer 502 and the one or more silicon-germanium layers 302, wherein silicon in the one or more silicon-germanium layers 302 can be oxidized (e.g., thereby forming silicon dioxide layers 506).

Further, the method 900 can comprise surrounding the column with a dielectric layer 106. The dielectric layer 106 can be, for example, silicon oxide (e.g., silicon dioxide). The surrounding at 904 can comprise depositing the dielectric layer 106 onto the one or more columns (e.g., one or more nanofluidic channel columns 104) and/or the semiconductor substrate 102 as illustrate and/or described herein with regards to FIGS. 6A and/or 6B.

At 904, the method 900 can comprise etching the column to remove the first silicon-germanium layer (e.g., concentrated silicon-germanium layer 504) and the second silicon-germanium layer (e.g., concentrated silicon-germanium layer 504). The etching at 904 can form a first nanofluidic channel 108 at a position of the first silicon-germanium layer (e.g., concentrated silicon-germanium layer 504) in the one or more columns (e.g., one or more nanofluidic channel columns 104). Also, the etching can further form a second nanofluidic channel 108 at a position of the second silicon-germanium layer (e.g., concentrated silicon-germanium layer 504) in the one or more columns (e.g., one or more nanofluidic channel columns 104). For example, the etching at 904 can comprise one or more selective etching processes to remove the one or more concentrated silicon-germanium layers 504, which can be formed by the annealing process, as described herein with regards to FIG. 6B.

Additionally, the method 900 can further comprise etching the dielectric layer 106 to form a first reservoir 202 and/or a second reservoir 204. The dielectric layer 106 can surround the first reservoir 202 and/or the second reservoir 204 as illustrated and/or described herein with regard to FIG. 2. For example, the plurality of nanofluidic channels 108 can extend from the first reservoir 202 to the second reservoir 204. Further, the method 900 can comprise thermal treating the one or more columns (e.g., one or more nanofluidic channel columns 104) to oxidize the silicon layers 110. Wherein the dielectric layer 106 is silicon dioxide, the one or more silicon layers 110 can become a part of dielectric layer 106 as a result of the thermal treatment, as illustrated and/or described herein with regard to FIG. 8.

Figure 10:
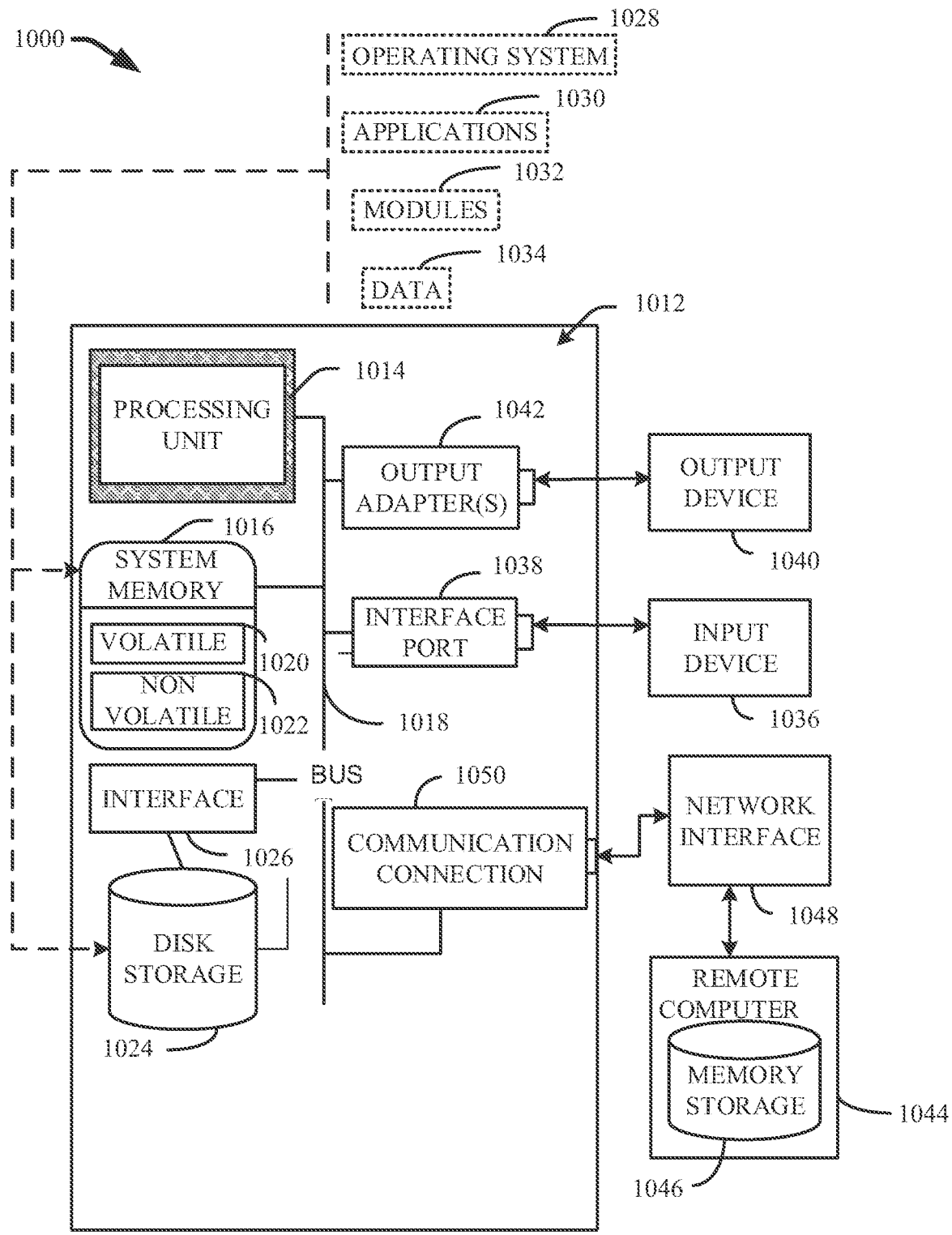
FIG. 10 illustrates a block diagram of an example, non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity. With reference to FIG. 10, a suitable operating environment 1000 for implementing various aspects of this disclosure can include a computer 1012. The computer 1012 can also include a processing unit 1014, a system memory 1016, and a system bus 1018. The system bus 1018 can operably couple system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, can be stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface can be used, such as interface 1026. FIG. 10 also depicts software that can act as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 can take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through one or more input devices 1036. Input devices 1036 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1014 through the system bus 1018 via one or more interface ports 1038. The one or more Interface ports 1038 can include, for example, a serial port, a parallel port, a game port, and a universal serial bus (USB). One or more output devices 1040 can use some of the same type of ports as input device 1036. Thus, for example, a USB port can be used to provide input to computer 1012, and to output information from computer 1012 to an output device 1040. Output adapter 1042 can be provided to illustrate that there are some output devices 1040 like monitors, speakers, and printers, among other output devices 1040, which require special adapters. The output adapters 1042 can include, by way of illustration and not limitation, video and sound cards that provide a means of connection between the output device 1040 and the system bus 1018. It should be noted that other devices and/or systems of devices provide both input and output capabilities such as one or more remote computers 1044.

Computer 1012 can operate in a networked environment using logical connections to one or more remote computers, such as remote computer 1044. The remote computer 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer 1044. Remote computer 1044 can be logically connected to computer 1012 through a network interface 1048 and then physically connected via communication connection 1050. Further, operation can be distributed across multiple (local and remote) systems. Network interface 1048 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus, comprising:
   a semiconductor substrate;
   a dielectric layer adjacent to the semiconductor substrate, the dielectric layer comprising a first nanofluidic channel and a second nanofluidic channel, wherein the second nanofluidic channel is located between the first nanofluidic channel and the semiconductor substrate, wherein the dielectric layer forms a first side of the first nanofluidic channel and a second side of the first nanofluidic channel; and
   a first silicon layer that forms a third side of the second nanofluidic channel, wherein the third side of the second nanofluidic channel is parallel with the semiconductor substrate, and wherein the dielectric layer is provided on a plurality of sides of the first silicon layer.

2. The apparatus of claim 1, wherein the dielectric layer is a silicon dioxide layer.

3. The apparatus of claim 1, further comprising:
   a first reservoir having a first parameter defined by the dielectric layer; and
   a second reservoir having a second parameter defined by the dielectric layer, wherein the first nanofluidic channel extends from the first reservoir to the second reservoir, and wherein the second nanofluidic channel extends the first reservoir to the second reservoir.

4. The apparatus of claim 1, wherein the semiconductor substrate forms a first side of the second nanofluidic channel.

5. The apparatus of claim 1, wherein the dielectric layer further forms a first side of the second nanofluidic channel and a second side of the second nanofluidic channel.

6. The apparatus of claim 1, further comprising:
   a second silicon layer that forms a third side of the first nanofluidic channel, wherein the dielectric layer is provided on a plurality of sides of the second silicon layer, wherein the third side of the first nanofluidic channel is parallel with the semiconductor substrate.

7. The apparatus of claim 1, wherein the first silicon layer further forms a third side of the first nanofluidic channel.

8. The apparatus of claim 1, wherein the dielectric layer is silicon dioxide.

9. An apparatus, comprising:
- a semiconductor substrate;
- a dielectric layer positioned adjacent to the semiconductor substrate;
- a first nanofluidic channel that traverses through the dielectric layer;
- a second nanofluidic channel that traverses through the dielectric layer, wherein the second nanofluidic channel is positioned between the first nanofluidic channel and the semiconductor substrate; and
- a silicon layer positioned between the first nanofluidic channel and the second nanofluidic channel, wherein the silicon layer forms a first side of the second nanofluidic channel opposite the semiconductor substrate.

10. The apparatus of claim 9, wherein the dielectric layer forms a perimeter of the first nanofluidic channel.

11. The apparatus of claim 9, wherein the dielectric layer is silicon dioxide.

12. The apparatus of claim 9, wherein the first nanofluidic channel and the second nanofluidic channel are comprised within a plurality of nanofluidic channels that traverse the dielectric layer, and wherein a density of the plurality of nanofluidic channels within the dielectric layer is greater than or equal to 100 per square micrometer and less than or equal to 10,000 per square micrometer.

* * * * *